US00PP17614P2

(12) United States Plant Patent
van der Knaap

(10) Patent No.: US PP17,614 P2
(45) Date of Patent: Apr. 17, 2007

(54) ***KALANCHOE* PLANT NAMED 'DON RAMON'**

(50) Latin Name: *Kalanchoe blossfeldiana*
Varietal Denomination: Don Ramon

(75) Inventor: Leonardus Johannus Maria van der Knaap, Naaldwijk (NL)

(73) Assignee: Knaap Licenties B.V., Naaldwijk (NL)

( * ) Notice: Subject to any disclaimer, the term of this patent is extended or adjusted under 35 U.S.C. 154(b) by 0 days.

(21) Appl. No.: 11/259,306

(22) Filed: Oct. 26, 2005

(51) Int. Cl.
*A01H 5/00* (2006.01)

(52) U.S. Cl. ..... Plt./335

(58) Field of Classification Search ..... Plt./335
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Kalanchoe* plant named 'Don Ramon', characterized by its upright and freely branching plant habit; dark green-colored leaves; red purple-colored double flowers with multiple petals per flower; and excellent postproduction longevity.

1 Drawing Sheet

Botanical designation: *Kalanchoe blossfeldiana.*
Cultivar denomination: 'Don Ramon'.

BACKGROUND OF THE INVENTION

The present invention relates to a new and distinct cultivar of *Kalanchoe* plant, botanically known as *Kalanchoe blossfeldiana,* and hereinafter referred to by the name 'Don Ramon'.

The new *Kalanchoe* is a product of a planned breeding program conducted by the Inventor in Naaldwijk, The Netherlands. The objective of the breeding program was to create new freely-flowering *Kalanchoe* cultivars with multiple flower petals, attractive flower coloration and excellent postproduction longevity.

The new *Kalanchoe* originated from a cross-pollination made in Naaldwijk, The Netherlands on May 26, 2003, of a proprietary selection of *Kalanchoe blossfeldiana* identified as code number 2000033, not patented, as the female, or seed, parent with a proprietary selection of *Kalanchoe blossfeldiana* identified as code number 20000282-2, not patented, as the male, or pollen, parent. The new *Kalanchoe* was discovered and selected by the Inventor as a single flowering plant within the progeny of the stated cross-pollination grown in a controlled environment in Naaldwijk, The Netherlands on Apr. 12, 2004.

Asexual reproduction of the new *Kalanchoe* by terminal cuttings at Naaldwijk, The Netherlands, has shown that the unique features of this new *Kalanchoe* are stable and reproduced true to type in successive generations.

BRIEF SUMMARY OF THE INVENTION

The cultivar Don Ramon has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Don Ramon'. These characteristics in combination distinguish 'Don Ramon' as a new and distinct cultivar:

1. Upright and freely branching plant habit.
2. Dark green-colored leaves.

3. Red purple-colored double flowers with multiple petals per flower.
4. Excellent postproduction longevity.

Plants of the new *Kalanchoe* differ primarily from plants of the female parent selection primarily in leaf shape as plants of the female parent selection have entire leaf margins.

Plants of the new *Kalanchoe* differ from plants of the male parent selection in the following characteristics:

1. Plants of the new *Kalanchoe* have darker green-colored leaves than plants of the male parent selection.
2. Plants of the new *Kalanchoe* have double flowers whereas plants of the male parent selection have single flowers.
3. Plants of the new *Kalanchoe* and the male parent selection differ in flower color as plants of the male parent selection have white-colored flowers.

Plants of the new *Kalanchoe* can be compared to plants of the *Kalanchoe* cultivar Don Frederico, disclosed in a U.S. Plant patent application Ser. No. 11/259,309. In side-by-side comparisons conducted in Naaldwijk, The Netherlands, plants of the new *Kalanchoe* differed from plants of the cultivar Don Frederico in the following characteristics:

1. Plants of the new *Kalanchoe* had longer petals than plants of the cultivar Don Frederico.
2. Plants of the new *Kalanchoe* had red purple-colored flowers whereas plants of the cultivar Don Frederico had yellow-colored flowers.

BRIEF DESCRIPTION OF THE PHOTOGRAPHS

The accompanying colored photographs illustrate the overall appearance of the new *Kalanchoe,* showing the colors as true as it is reasonably possible to obtain in colored reproductions of this type. Colors in the photographs may differ slightly from the color values cited in the detailed botanical description which accurately describe the colors of the new *Kalanchoe.*

The photograph at the top of the sheet comprises a side perspective view of a typical flowering potted plant of 'Don Ramon'.

The photograph at the bottom of the sheet comprises a close-up view of a typical flowering plant of 'Don Ramon'.

DETAILED BOTANICAL DESCRIPTION

In the following description, color references are made to The Royal Horticultural Society Colour Chart, 2001 Edition, except where general terms of ordinary dictionary significance are used. Plants used in the photographs and for the following observations and measurements were grown in Naaldwijk, The Netherlands, under commercial practice in a glass-covered greenhouse for about 14 weeks after planting with day temperatures ranging from 20° C. to 30° C., night temperatures ranging from 18° C. to 25° C. and light levels ranging from 5 to 60 kilolux. Plants used in the description and photographs were not pinched.

Botanical classification: *Kalanchoe blossfeldiana* cultivar Don Ramon.

Parentage:

*Female, or seed, parent.*—Proprietary selection of *Kalanchoe blossfeldiana* identified as code number 2000033, not patented.

*Male, or pollen, parent.*—Proprietary selection of *Kalanchoe blossfeldiana* identified as code number 20000153-2, not patented.

Propagation:

*Type cutting.*—Terminal cuttings.

*Time to initiate roots, summer.*—About ten days at 21° C.

*Time to initiate roots, winter.*—About 14 days at 21° C.

*Time to produce a rooted young plant, summer.*—About three weeks at 21° C.

*Time to produce a rooted young plant, winter.*—About four weeks at 21° C.

*Root description.*—Fine, fibrous; white in color.

*Rooting habit.*—Freely branching.

Plant description:

*Form/growth habit.*—Upright and rounded plant habit; freely flowering habit with numerous compound cymes. Actual plant shape will depend on whether or not plants are pinched (terminal apices removed). Vigorous growth habit.

*Branching habit.*—About 15 lateral branches per plant. Pinching is not required but will enhance lateral branch development.

*Plant height at flowering.*—About 18 cm.

*Plant diameter at flowering.*—About 32 cm.

*Lateral branch description.*—Length: About 8 cm to 15 cm. Diameter: About 5 mm. Internode length: About 5 mm. Strength: Strong. Texture: Smooth, glabrous. Color: 146B.

*Foliage description.*—Arrangement: Opposite, simple. Length: About 5 cm to 13 cm. Width: About 3 cm to 8.5 cm. Shape: Ovate. Apex: Broadly acute. Base: Acute. Margin: Crenate. Texture, upper and lower surfaces: Smooth, glabrous; leathery; succulent. Venation pattern: Pinnate; reticulate. Color: Developing foliage, upper surface: Between 137A and 146A. Developing foliage, lower surface: 146A to 146B. Fully expanded foliage, upper surface: 147A; venation, 146A. Fully expanded foliage, lower surface: 147B; venation, 147B. Petiole length: About 1 cm to 2.5 cm. Petiole diameter: About 8 mm. Petiole texture, upper and lower surfaces: Smooth, glabrous. Petiole color, upper and lower surfaces: 146B.

Flower description:

*Flower type and habit.*—Double flowers with multiple petals arranged in compound dichasial cymes that arise from leaf axils. Freely flowering habit. Flowers persistent.

*Natural flowering season.*—Flowering year-round when flower initiation and development is induced under short day/long night conditions.

*Time to flower.*—About ten weeks with short day/long night conditions are required to produce flowering plants. Time to flower is primarily dependent upon temperature and light intensity.

*Post-production longevity.*—Plants of the new *Kalanchoe* maintain good leaf and flower substance for about four to six weeks under interior environmental conditions.

*Cyme height.*—About 4 cm to 7.5 cm.

*Cyme diameter.*—About 5 cm to 6 cm.

*Flowering habit.*—Freely flowering, potentially about 120 to 180 flowers per plant.

*Flower buds.*—Shape: Ovoid. Length: About 9 mm. Width: About 3 mm. Color: 145C; towards the apex, 54C.

*Flower diameter.*—About 1.5 cm.

*Flower depth (height).*—About 1.4 cm.

*Petals.*—Quantity: About 15 per flower. Length: About 1.5 cm. Width: About 5 mm. Shape: Spatulate. Apex: Apiculate. Base: Fused. Margin: Entire. Texture, upper and lower surfaces: Glabrous, smooth. Color: When opening, upper surface: Between N57A and 61B. When opening, lower surface: 62B. Fully opened, upper surface: Close to N66A; color becoming closer to N66A to N66B with development. Fully opened, lower surface: 62B to 62C.

*Sepals.*—Quantity: About four per flower. Length: About 5 mm. Width: About 1 mm. Shape: Lanceolate. Apex: Acute. Base: Fused. Margin: Entire. Texture, upper and lower surfaces: Glabrous, smooth. Color: When opening and fully opened, upper surface: 144A. When opening and fully opened, lower surface: 144A.

*Peduncles.*—Length: About 13 cm. Diameter: About 2 mm to 4 mm. Angle: Erect to about 45° from vertical. Strength: Moderately strong. Texture: Smooth, glabrous. Color: 144B.

*Pedicels.*—Length: About 5 mm. Diameter: About 1 mm. Angle: Erect to about 45° from vertical. Strength: Moderately strong. Texture: Smooth, glabrous. Color: 146C.

*Reproductive organs.*—Stamens: Stamen number: About eight per flower. Anther length: About 1 mm. Anther shape: Oval. Anther color: 151B. Pollen amount: None observed. Pistils: Pistil number: About four per flower. Pistil length: About 8 mm. Style length: About 2 mm. Style color: 144D. Stigma shape: Round. Stigma color: 151D. Ovaries: Superior and four-celled. Ovary color: 144B.

*Seeds.*—Seed development has not been observed.

Disease/pest resistance: Resistance to known pathogens and pests common to *Kalanchoe* has not been observed on plants of the new *Kalanchoe* grown under commercial greenhouse conditions.

Temperature tolerance: Plants of the new *Kalanchoe* have been observed to tolerate temperatures from 5° C. to 35° C.

It is claimed:

1. A new and distinct cultivar of *Kalanchoe* plant named 'Don Ramon', as illustrated and described.

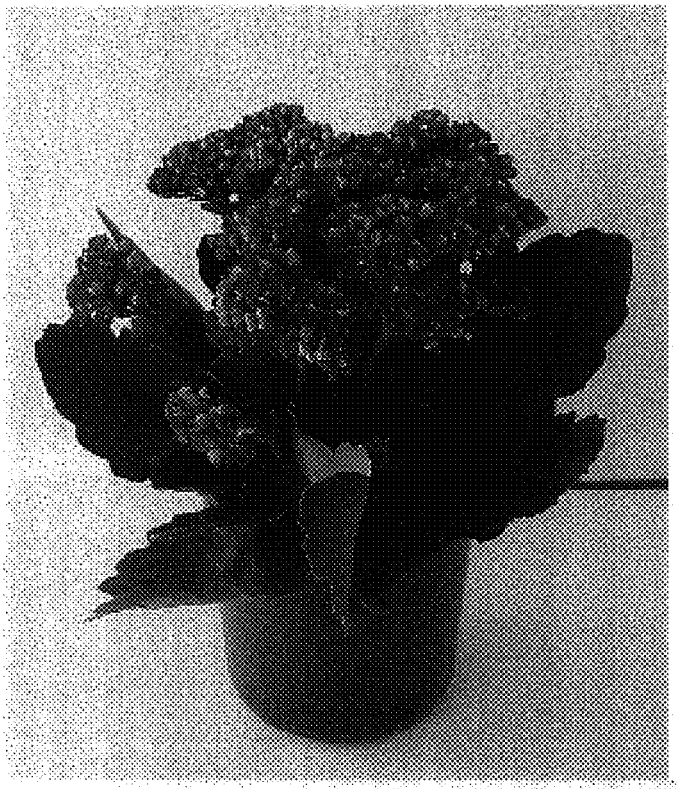
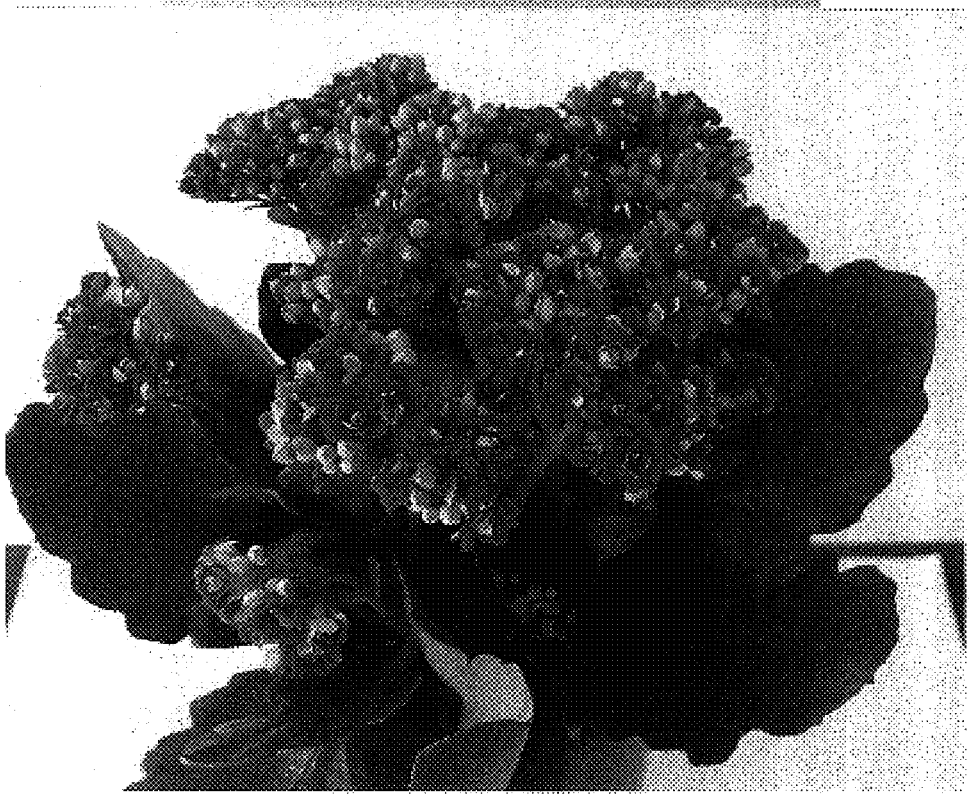

* * * * *